United States Patent
Paradisi et al.

(10) Patent No.: US 7,297,777 B2
(45) Date of Patent: Nov. 20, 2007

(54) PROCESS OF PURIFICATION OF HCG AND RECOMBINANT HCG PURIFIED BY THAT METHOD

(75) Inventors: Gianfranco Paradisi, Monterotondo (IT); Mara Rossi, Rome (IT); Laura Scaglia, Rome (IT)

(73) Assignee: Laboratoires Serono SA, Coinsins, Vaud (CH)

( * ) Notice: Subject to any disclaimer, the term of this patent is extended or adjusted under 35 U.S.C. 154(b) by 563 days.

(21) Appl. No.: 10/204,630

(22) PCT Filed: Jan. 22, 2001

(86) PCT No.: PCT/EP01/00665

§ 371 (c)(1),
(2), (4) Date: Dec. 9, 2002

(87) PCT Pub. No.: WO01/62773

PCT Pub. Date: Aug. 30, 2001

(65) Prior Publication Data
US 2003/0104553 A1 Jun. 5, 2003

(30) Foreign Application Priority Data
Feb. 22, 2000 (EP) ................. 00103690

(51) Int. Cl.
*A61K 38/24* (2006.01)
*C07K 1/18* (2006.01)

(52) U.S. Cl. ...................... 530/399; 530/355
(58) Field of Classification Search ............ None
See application file for complete search history.

(56) References Cited

U.S. PATENT DOCUMENTS 6,583,109 B1 * 6/2003 Gallo et al. ............ 514/2

FOREIGN PATENT DOCUMENTS

| EP | 0 571 337 A2 | 11/1993 |
|---|---|---|
| WO | WO 90/09800 | 9/1990 |
| WO | 96/29095 A1 | 9/1996 |
| WO | WO 98/56806 | 12/1998 |

OTHER PUBLICATIONS

Huth et al., J. Biol. Chem., 267(13):8870-8879, 1992.*
Albert, Alexander, Journal of Clinical Endocrinology and Metabolism, 1969; 29: 1504-9.*
Bassett et al. Current medical research and opinion, 2005; 21: 1969-76.*
Huth et al., Bacterial expression and in vitro folding of the β-subunit of human chorionic gonadotropin (hCGβ) and functional assembly of recombinant hCGβ with hCGα, *Endocrinology*, 185(3):911-918 (1994).
Chen et al., Recombinant carbohydrate variant of human choriogonadotropin β-subunit (hCGβ) descarboxyl terminus (115-145), *The Journal of Biological Chemistry*, 266(10)6246-6251 (1991).
Dyr et al. Separation used for purification of recombiant proteins, *Journal of Chromatography B.*, 699:383-401 (1997).
Barnthouse et al., Cation-exchange displacement chromatography for the purification of recombinant protein therapeutics from variants, *Journal of Biotechnology*, 66:125-136 (1998).
Vydac, Analysis and purification of proteins and peptides by reversed-phase HPLC, A1486 (1998).
Lapthorn et al., Crystal structure of human chorionic gonadotropin, *Nature*, 369:455-461.
Cortvrindt et al., Recombinant luteinizing hormone as a survival and differentiation factor increases oocyte maturation in recombinant follicle stimulating hormone-supplemented mouse preantral follicle culture, *Human Reproduction*, 13(5)1292-1302 (1998).
Loumaye et al., Clinical assessment of human gonadotrophins produced by recombinant DNA technology, Sinapore Journal of Obstetrics and Gynecology, 27(1):36-43 (Abstract) (1996).

* cited by examiner

*Primary Examiner*—Elizabeth C. Kemmerer
*Assistant Examiner*—Christina Borgeest
(74) *Attorney, Agent, or Firm*—Browdy & Neimark, PLLC

(57) ABSTRACT

A process for the purification of recombinant human Chorionic Gonadotropin (hCG) from a sample of crude recombinant hCG in the supernatant of CHO cells comprises the combined use of ion-exchange chromatography and reverse phase HPLC. The ion-exchange chromatography is performed twice and the final use of a size exclusion chromatography allows the purification from any residual traces of contaminants. The specific bioactivity of the highly purified hCG obtained form the process is particularly high, amounting to about 25,000 IU/mg.

7 Claims, No Drawings

PROCESS OF PURIFICATION OF HCG AND RECOMBINANT HCG PURIFIED BY THAT METHOD

CROSS-REFERENCE TO RELATED APPLICATIONS

This application is a 371 national stage of PCT/EP01/00665 filed Jan. 22, 2001, which claims priority to EP 00103690.4 filed Feb. 22, 2000.

FIELD OF INVENTION

The present invention relates to a process for the purification of Chorionic Gonadotropin, in particular the purification of recombinant human Chorionic Gonadotropin (hCG) from a sample of crude recombinant hCG. The method comprises the use of ion-exchange chromatography and reverse phase HPLC.

Chorionic gonadotropin is a hormone produced by the placenta and traditionally obtained from the urine of pregnant women.

The hormone is a heterodimer consisting of non-covalently bound α and β subunits. Its effects are predominantly those of the gonadotropin luteinising hormone.

Chorionic gonadotropin is given to women to induce ovulation after follicular development has been stimulated with follicle-stimulating hormone or human menopausal gonadotropins in the treatment of anovulatory infertility due to absent or low concentrations of gonadotropins. A single dose of 5000 to 10000 units is given by intramuscular injection to mimic the midcycle peak of luteinising hormone which normally stimulates ovulation. Chorionic gonadotropin is also given in conjunction with menotrophin and sometimes also clomiphene citrate as an adjunct to in vitro fertilisation procedures and other assisted conception techniques involving superovulation and oocyte collection. In males it has been used in the treatment of prepubertal cryptorchidism. Regimens vary widely, but doses usually range from 500 to 4000 units three times weekly by intramuscular injection.

It is also given for male infertility associated with hypogonadotrophic hypogonadism Again, there is considerable variation in the dosage regimen, and doses have varied from 500 to 4000 units two to three times weekly. An agent with follicle-stimulating activity such as menotrophin is often added to enable normal spermatogenesis. For oligospeia, doses of up to 3000 units of chorionic gonadotropin weekly with menotrophin or another follicle-stimulating preparation may be employed. In the treatment of delayed puberty associated with hypogonadism in males, a dose of 500 to 1500 units is given twice weekly; the dose should be titrated against plasma-testosterone concentration.

Different methods have been used to isolate and purify hCG from raw urine samples (Birken et al., Endocrinology, 133(3): 1390-7, 1993; Sakakibara et al., Chem. Pharm. Bull., 35(5): 1414-6, 1990; Donini et al., Acta Endocrinol., 73(1): 133-45, 1973). Recently, a different method of affinity chromatography, termed membrane filtration affinity chromatography, has been developed and applied to purify hCG from urine (Xu et al., Protein expression and purification, 16: 221-3, 1999). The method avoids the use of BrCN activated Sepharose as a solid-phase for the affinity chromatography column and represents a variation of the usual methods of purification of hCG by affinity chromatography from urine samples. Immunoactivity of the purified hCG according to this method is 8554 IU/mg.

Recombinant hCG has the advantage of being devoid of other gonadotropin hormones and contaminants of human origin and more specifically of those present in human urine. The crude preparation of recombinant hCG contains, however, all other proteins and contaminants of the cell used in its recombinant production and a method for achieving an absolute purity of recombinant Chorionic Gonadotropin is highly desirable.

SUMMARY OF THE INVENTION

We have now found that a crude preparation of hCG, deriving from a concentrated sample of a culture medium obtained after the recombinant process or from a crude concentrate of urine of pregnant women, can be purified such that the resulting hCG is practically free from proteins or other contaminants contained in the crude hCG preparation.

The purification process is based on the use of ion-exchange chromatography and reverse phase HPLC. The possible further use of a size exclusion column allows the removal of any residual traces of contaminants. Optimum results are obtained when at least two steps of ion-exchange chromatography are performed.

The process of the invention can be used for the purification of recombinant hCG from a crude preparation of the culture medium derived from the recombinant process. The r-hCG is obtained with a high degree of purity and high specific bioactivity (in the range of 23,000-28,000 IU/mg), practically free from Foetal Bovine Serum (FBS) proteins, if present in the culture medium, and from nucleic acids or other contaminants contained in the host cells used in the recombinant process.

The process of the invention can be used as well for the purification of urinary hCG, starting from a crude concentrate of urine of pregnant women, and for the purification of CG from other mammalian species including, for example, bovine, equine, porcine, ovine and monkey.

It is an object of the present invention to provide a process for purification of hCG from a sample comprising the use of ion-exchange chromatography and reverse phase HPLC.

The process comprises the steps of subjecting the sample to ion-exchange chromatography and subjecting the eluate to reverse phase HPLC. A further step of applying the eluate to a size exclusion column may additionally be carried out.

The two ion-exchange chromatography steps are preferably performed under different conditions in order to obtain optimum results from the purification process. A preferred embodiment of the process of the invention comprises the steps of:

(a) eluting the sample through a silica chromatography column;

(b) eluting through a DEAE SEPHAROSE (cross-linked agarose matrix with diethylaminoethyl weak anion exchanger) ion-exchange chromatography column;

(c) eluting through a CM-SEPHAROSE (cross-linked agarose matrix with carboxymethyl weak anion exchanger) ion-exchange chromatography column;

(d) eluting through a Silica C18 reverse phase HPLC column.; and (e) eluting through a CM-SEPHACRYL (spherical allyl dextran and N,N'-methylenebisacrylamide) size exclusion chromatography column.

In a preferred embodiment of the invention, elution through the DEAE SEPHAROSE ion-exchange column is carried out in sodium phosphate buffer at about pH 7,5.

Elution through the CM-SEPHAROSE (cross-linked agarose matrix with carboxymethyl weak anion exchanger) ion-exchange column is preferably carried out in sodium phosphate buffer at about pH 6.

The reverse phase HPLC step (d) is preferably carried out with 2-propanol/Tris-phosphate buffer as mobile phase.

The CG of the present invention is preferably human CG and most preferably is recombinant hCG, deriving from the culture medium of CHO cells used in the recombinant process.

It is a further object of the present invention to provide a pharmaceutical composition comprising a therapeutically effective amount of purified recombinant hCG as prepared by the recombinant process as described above, together with suitable excipients. An example of a suitable excipient is sucrose, which aids in the stabilisation of the lyophilised product. The pharmaceutical composition of recombinant hCG is particularity suitable for subcutaneous administration.

DETAILED DESCRIPTION OF THE INVENTION

The invention provides a method for the purification of hCG, in particular for the purification of recombinant hCG from a crude preparation of the culture medium of the recombinant process. The r-hCG is obtained with a high degree of purity and high specific bioactivity (in the range of 23,000-28,000 IU/mg), practically free from Foetal Bovine Serum (FBS) proteins which are present in the culture medium and from nucleic acids or other contaminants contained in the host cells used in the recombinant process.

The invention is intended for use with biological materials, particularly crude mixtures containing hCG and other contaminating proteins referred to herein as starting material samples. The examples described in detail below use starting material samples containing r-hCG obtained from cell culture supernatant medium from a bioreactor. Alternatively, the sample is crude concentrated urine from pregnant women.

The sample is constituted by freshly collecting cell culture supernatant medium perfused through a bioreactor over two days. Preferably the supernatant is clarified by filtration. If necessary, the crude solution is concentrated and subjected to C4 silica chromatography to remove contaminants derived from the cell culture.

The semi-purified harvest, after ultrafiltration, is then subject to ion-exchange chromatography, which is preferably performed twice, and preferably under different conditions, and to reverse phase HPLC. A first DEAE SEPHAROSE ion-exchange step may be performed, essentially acting as an hCG "flow through" step, in which a large part of the non-hCG proteins and DNA are eliminated. A second ion-exchange step, preferably through a CM-SEPHAROSE column, acts as an hCG binding step, and removes residual DNA and host cell or medium protein contaminants. In a preferred embodiment this step is performed at about 5° C. eluting with sodium phosphate buffer at about pH 6.

Reverse phase chromatography on a Silica C18 column is effective in removing trace amounts of nucleic acids and cell culture derived contaminants. The column is preferably eluted with 2-propanol/Tris-phoshate buffer as mobile phase. The retentate solution is preferably then subjected to 10 kD cut-off ultrafiltration, concentrated and can be recovered with ammonium hydrogen carbonate pH 8. The concentrated product can then be applied to a size exclusion chromatography column on SEPHACRYL S200 HR. In this step, a separation based on molecular size is achieved eluting with ammonium hydrogen carbonate pH 8 to remove still possible trace amounts of cell culture derived contaminants, potential aggregates and free hCG sub-units. The eluate can then undergo a dialysis by ultrafiltration on membranes with 10 kD cut-off, preferably in sodium phosphate buffer, pH 7. After filtration, the purified hCG bulk is preferably stored in sterile bottles at low temperature.

EXAMPLE 1

Reagents:

Ammonia, analytical grade

Ammonium hydrogen carbonate, analytical grade (B.P.)

Di-sodium hydrogen phosphate, analytical grade

Absolute denatured Ethanol,

Phosphoric acid, analytical grade (Ph.Eur.)

2-propanol, analytical grade (Ph.Helv.)

Sodium chloride, analytical grade (Ph.Eur.)

Sodium di-hydrogen phosphate, analytical grade

Sodium hydroxide pellets, analytical grade (Ph.Eur.)

Trifluoroacetic acid (TFA), HPLC grade

Tris-(hydroxymethyl) aminomethane, analytical grade

Purification Process Summary Flow Diagram

Harvest material derived from the cell culture process is purified and concentrated by a series of five chromatographic steps.

The following flow diagram (Table 1) summarises a preferred embodiment of the r-hCG purification process, outlining the chromatographic column resins and the principles of operation of each of the intermediate steps.

TABLE 1

Flow diagram summarising the r-hCG purification process.

| | |
|---|---|
| Step I | CULTURE MEDIUM FROM BIOREACTOR |
| | C4 silica chromatography |
| | (Eluate contains r-hCG) |
| | Ultrafiltration 10 kD cut-off |
| | (Retentate contains r-hCG) |
| | CONCENTRATED CRUDE r-hCG HARVEST |
| Step II | DEAE SEPHAROSE FF |
| | (Unbound fraction contains r-hCG) |
| Step III | CM SEPHAROSE FF |
| | (Eluate contains r-hCG) |
| Step IV | RP-HPLC ON SILICA C18 |
| | (Eluate contains r-hCG) |
| | Ultrafiltration (10 kD) |
| Step V | SEPHACRYL S-200 HR |
| | (Eluate contains r-hCG) |
| | r-hCG BULK SOLUTION |

A detailed flow diagram and process description are provided below. The conditions given for the capture step (step I) are those which are normally applied when the crude material is of recombinant origin.

Step I (Capture Step)

In this step (Step I), a preliminary concentration is achieved and the buffer is changed to be of controlled composition. This step is initiated at room temperature (Silica C4 chromatography) and then continued at about +5° C. A preferred temperature range is 5±3. It is repeated individually for each harvest during the production cycle of the bioreactor.

(i) Clarification of Harvests

The freshly collected culture medium from the bioreactor is usually first clarified by filtration.

(ii) Silica C4 Chromatography

After clarification, the harvests are loaded onto a C4 silica chromatography column, which has been previously equilibrated in sodium phosphate 25 mM, pH 7. A preferred pH range is from 6.6 to 7.7. The column is washed with sodium phosphate 25 mM until the UV monitor signal returns to baseline. The product is then eluted with 34.2% ($^w/_w$) 2-propanol in sodium phosphate 25 mM.

(iii) Ammonia Treatment

Ammonia is then added to the solution to reach a final concentration of 1 M. This mixture is incubated for 6. hours. Then the solution is 2 fold diluted with water, and the pH is adjusted to 7.5 using phosphoric acid 85%. A preferred pH range is 7.5±0.2.

(iv) Concentration and Dialysis

The 10 kD cut-off membranes stored in 0.05 M sodium hydroxide between batches are rinsed with purified water until the pH descends to approximately 8.

The product is concentrated and dialysed (by ultrafiltration on the 10 kD membrane) to remove material having molecular weight lower than 10 kD and to eliminate traces of 2-propanol and to change the ammonia solution to sodium phosphate 40 mM pH 7.5. A preferred pH range is 7.5±0.2

The final retentate is recovered from the membranes with sodium phosphate 40 mM in order to achieve a target protein concentration of 3 to 15 mg/ml.

The solution is then filtered and the resulting concentrate is stored frozen at about −15° C.

Step II (Filtration and Ion exchange on DEAE SEPHAROSE FF Chromatography)

This chromatography step is an r-hCG "flow-through" step in which a large part of the non r-hCG proteins and nucleic acids are eliminated. Whilst the filtration is carried out at room temperature, the chromatography stage where product passes through the column, is carried out in a cold room.

(i) Thawing and Pooling of the r-hCG Concentrated Crude Harvests

The frozen concentrates are thawed and pooled. A batch of purified bulk r-hCG is processed from a pool of a variable number of r-hCG crude concentrates produced from the same working cell bank. The criteria for the number of r-hCG crude concentrates pooled is based on the maximum protein binding capacity of the next chromatographic step in the purification process (4 mg total protein/mg of resin).

(ii) Clarification by Filtration

The r-hCG solution is preferably passed through a filter apparatus and the filters washed with 40 mM sodium phosphate pH 7.5.

The filtered solution and washes are pooled.

(iii) Ion Exchange Chromatography on DEAE SEPHAROSE FF

The column, packed with a weakly charged anion-exchange resin, diethyl amino ethane (DEAE) SEPHAROSE Fast Flow, is equilibrated with 40 mM sodium phosphate (pH 7.5)

The r-hCG solution is loaded onto the column.

The column is fed with 40 mM sodium phosphate pH 7.5. The chromatographic process is monitored by spectrophotometry at 280 nm.

The leading effluent is discarded until the peak starts eluting. The unbound fraction containing the r-hCG is then collected.

Step III (CM SEPHAROSE FF Chromatography)

In this chromatographic step, a large part of the host cells contaminants are removed. The chromatographic step is carried out about 5° C. A preferred temperature range is 5±3.

(i) Dilution of the DEAE SEPHAROSE FF Eluate Water for injection is added to the DEAE SEPHAROSE FF eluate and the pH adjusted to 6 using phosphoric acid 85%. A preferred pH range is 6±0.1.

(ii) Ion Exchange Chromatography on CM SEPHAROSE FF

The column, packed with a weakly charged cation-exchange resin, Carboxymethyl (CM) SEPHAROSE Fast Flow, is equilibrated with 20 mM sodium phosphate buffer (pH 6). A preferred pH range is 6 0.1.

The r-hCG solution is loaded onto the column.

The column is washed with 20 mM sodium phosphate buffer pH 6. The chromatographic process is monitored by spectrophotometry at 280 nm.

The product is eluted using 130 mM sodium phosphate buffer pH 6. The leading effluent is discarded until the peak starts eluting.

The entire peak containing the r-hCG is collected. The product can be optionally filtered at this stage to remove viral contaminants.

Step IV (RP-HPLC on Silica C18)

This RP-HPLC chromatographic step is effective in removing trace amounts of cell culture contaminants, nucleic acid residues and endotoxins It is followed by a 10 kD cut-off ultafiltration and optional filtration.

(i) Preparation of the Aliquots

The pH of the aliquots is adjusted to 5 and 2-propanol is added to a final concentration of 15% ($^v/_v$).

(ii) RP-HPLC Chromatography on Silica C18.

The column, packed with a Silica C18 resin is first equilibrated in 15% ($^v/_v$) 2-propanol in Tris-phosphate 0.5 M buffer.

The first aliquot is loaded onto the column and the chromatography is monitored by UV spectrophotometry.

The column is washed with the same equilibration buffer.

Elution of the r-hCG is subsequently performed with a linear gradient of 2-propanol/Tris-phosphate 0.5 M buffer mobile phase from 15% to 25% ($^v/_v$).

The r-hCG is fractionated when the corresponding peak is detected by spectrophotometry ($A_{280}$). The fractions whose absorbance is greater than 65% of the maximum peak height at the ascending part and higher than 20% of the maximum peak height at the descending part are pooled.

The four r-hCG containing pools are then pooled and diluted in an equivalent volume of Water For Injection (WFI).

The product is concentrated and dialysed (by ultrafiltration on a 10 kD membrane) against WFI to remove material having molecular weight lower than 10 kD and to eliminate 2-propanol.

The product is then dialysed by ultrafiltration against ammonium hydrogen carbonate buffer 0.1 M, pH 8.

The resulting intermediate is stored at about +5° C. or frozen if required. Preferred storage temperatures are 5±3° C. and equal or below −15° C. respectively.

Step V (Size Exclusion Chromatography on SEPHACRYL S-200 HR)

This size exclusion chromatographic step is effective in removing trace amounts of cell culture derived contaminants, potential aggregates and/or free sub-units. It is followed by a 10 kD cut-off ultrafiltration. The Sephacryl S-200 HR and the 10 kD cut-off ultrafiltration steps are carried at about 5° C. A preferred temperature range is 5±3° C.

(i) Size Exclusion on Sephacryl S-200 HR.

The column packed with Sephacryl S-200 HR resin is equilibrated with Ammonium hydrogen carbonate 0.5 M (pH 8). A preferred pH range is 8±0.2.

The r-hCG soulution is loaded onto the column, and the elution intiated using Ammonium hydrogen carbonate 0.5 M, pH 8. A preferred pH rand is 8±0.2.

The collection of the r-hCG fraction is initiated from the beginning of the peak and lasts until the 50% mark of the maximum peak height at the descending part of the peak is reached.

(ii) 10 kD cut-off Ultrafiltration.

10 kD cut-off membranes stored in 0.05 M sodium hydroxide between batches are rinsed with WFI until the pH descends to approximately 8.

The product is concentrated and dialysed (by ultrafiltration) against WFI.

The product is then dialysed (by ultrafiltration) against Sodium phosphate buffer 0.01 M, pH 7, and the final protein concentration adjusted to reach a target final concentration of 3.5 mg/ml.

The resulting r-hCG final bulk solution is preferably stored frozen at about −15° C.

Chromatographic Resins

The following chromatographic resins may be employed in the purification process:

Equivalent resins can also be employed.

| | | |
|---|---|---|
| Step I: | Silica C4, 250 Ängstrom-50 μm | (Matrex ®, Millipore) |
| Step II: | DEAE SEPHAROSE FF | (Pharmacia) |
| Step III: | CM SEPHAROSE FF | (Pharmacia) |
| Step IV: | Silica C18, 300 angström-15–20 μm | (Vydac) |
| Step V: | SEPHACRYL S-200 HR | (Pharmacia) |
| | The current suppliers are: | |
| | Amersham Pharmacia Biotech, | Millipore Corporation |
| | Björkgatan 30 | 17 Cherry Hill Drive |
| | S-751 84, Uppsala | Danvers, MA 01923 |
| | Sweden | USA |
| | Vydac, The Separations Group, | |
| | 17434 Mojave St. | |
| | Hesperia, CA 92345 | |
| | USA | |

Results

Molecular Weight and Size

SDS-PAGE

The relative molecular weight of r-hCG obtained following the purification method of the present invention has been determined by SDS-PAGE against standard proteins of known molecular weight.

Coomassie brilliant blue staining after non-reducing SDS-PAGE revealed a single broad band for the r-hCG heterodimer at approximately molecular weight 70 kD (range 65-75 kD). The identity of the band was confirmed by Western blotting.

Biological Activity

Biological Activity of different batches of r-hCG after purification with the method of the present invention is reported in Table 2. The protein concentration has been determined by spectrophotometry at 276.5 nm, a=0.616.

The average specific activity of the r-hCG preparation is particularly high, amounting to about 25.000 IU/mg.

TABLE 2

| r-hCG batch | Specific bioactivity (IU/mg) |
|---|---|
| BCEA 9901 | 24427 |
| BCEA 9902 | 26868 |
| BCEA 9903 | 25636 |
| BCEA 9904 | 27152 |
| BCEA 9905 | 23729 |

Formulations

Both liquid and freeze dried formulations have been developed with the highly purified recombinant hCG of the present invention.

Liquid Formulation

Two liquid formulations at 10000 IU/ml were prepared in vials DIN 2R using mannitol or sucrose as excipient and submitted to stability tests at 50, 40, 25 and 4° C.

The composition is reported in tables 3 and 4.

TABLE 3

| Ingredients | UNIT | |
|---|---|---|
| r-hCG | IU/mL | 10000 |
| SUCROSE | mg/ml | 102.6 |
| O. PHOSPHORIC ACID | mg/ml | 0.98 |
| SODIUM HYDROXIDE | | q.s. to pH 7.0 |

Filling volume 0.5 ml

TABLE 4

| Ingredients | UNIT | |
|---|---|---|
| r-hCG | IU/ml | 10000 |
| MANNITOL | mg/ml | 54.6 |
| O. PHOSPHORIC ACID | mg/ml | 0.98 |
| SODIUM HYDROXIDE | | q.s. to pH 7.0 |

Filling volume 0.5 ml

The results of the stability tests, carried out by Bioassay, SE/HPLC and RP-HPLC, showed that the mannitol formulation was more stable with respect to the sucrose formulation. Refrigerated storage conditions were preferably required to minimise the protein oxidation and free subunit formation.

Freeze Dried Formulation

A freeze dried formulation at 5000 IU strength was prepared in vials DIN 2R for stability tests at 50, 40, 25 and 4° C. using sucrose as excipient.

The composition is reported in table 5.

TABLE 5

| Ingredients | UNIT | |
| --- | --- | --- |
| r-hCG | IU | 5000 |
| SUCROSE | mg | 30 |
| O-PHOSPHORIC ACID | mg | 0.98 |
| SODIUM HYDROXIDE | | q.s. to pH 7.0 |

The results of the stability tests, carried out by Bioassay, SE/HPLC and RP-HPLC, showed that this freeze dried formulation was stable at 40 and 50° C. at least for 19 weeks.

The stability tests at 25 and 4° C. were performed up to 6 months indicating no degradation of the active substance.

What is claimed is:

1. A process for the purification of recombinant human chorionic gonadotropin (hCG) from a sample containing recombinant hCG, comprising:
    (a) eluting the sample containing recombinant hCG through a silica chromatography column;
    (b) eluting the sample through an ion-exchange chromatography column;
    (c) eluting through a second ion-exchange chromatography column;
    (d) eluting through a reverse phase high performance liquid chromatography (HPLC) column; and
    (e) applying the eluate to a size exclusion chromatography column.

2. A process for the purification of recombinant hCG according to claim 1, from a sample containing recombinant hCC, wherein:
    the ion-exchange chromatography column of step (b) is a DEAE SEPHAROSE (cross-linked agarose matrix with die thylaminoethyl weak anion exchanger) ion-exchange chromat:ography column;
    the second ion-exchange chromatograph column of step (c) is a CM-SEPHAROSE (cross-linked agarose matrix with carboxymethylweak anion exchanger) ion-exchange chromatography column;
    the reverse phase HPLC column of step (d) is a Silica C18 reverse phase HPLC column; and the size exclusion chromatography column of step (e) is a SEPHACRYL (spherical allyl dextran and N,N'-methylenebisacrylamide) size exclusion chromatograph column.

3. A process according to claim 2, wherein elution thrbuqh the DEAE SEPHAROSE ion-exchange chromatography is carried out in sodium phosphate buffer at pH 7.5.

4. A process according to claim 2 or 3, wherein elution through the CM-SEPHAROSE ion-exchange chromatography is carried out in sodium phosphate buffer at pH 6.

5. A process according to claim 2 or 3, wherein the reverse phase HPLC step (d) is carried out with 2-propanol-trisphosphate buffer as mobile phase.

6. A process according to claim 2 or 3, wherein the size-exclusion chromatography step (e) is carried out wirh ammonium hydrogen carbonate buffer as mobile phase.

7. A process according to claim 2 or 3, wherein the sample containing recombinant hCG is a culture medium from rebombinant CHO cells that produce human chorionic gonadotropin.

* * * * *